United States Patent [19]

Oliver

[11] 4,321,834
[45] Mar. 30, 1982

[54] MECHANICAL STRESS GRADING OF TIMBER

[76] Inventor: George A. Oliver, 72 Lancaster Ave., Craighall Park, Johannesburg, South Africa

[21] Appl. No.: 147,222

[22] Filed: May 6, 1980

[30] Foreign Application Priority Data

May 7, 1979 [ZA] South Africa ............ 79/2170

[51] Int. Cl.³ ............................. G01N 3/32
[52] U.S. Cl. ............................. 73/812
[58] Field of Search ........... 73/852, 812, 849, 573, 73/574, 579, 582, 570, 808, 813, 816

[56] References Cited

U.S. PATENT DOCUMENTS 3,196,672 7/1965 Keller .................... 73/812
3,473,371 10/1969 Loeb .................... 73/816

OTHER PUBLICATIONS

U.S.D.A. Forest Service General Technical Report FPL7, Machine Stress . . . Producers, 1977, pp. 51–56 and 69–79.

Primary Examiner—Jerry W. Myracle
Attorney, Agent, or Firm—Murray and Whisenhunt

[57] ABSTRACT

A mechanical timber grading machine comprises inlet and outlet clamping stations for a length of timber. Each clamping station comprises a number of support and clamping rolls. Midway between the clamping stations is an oscillating station also comprising clamping and support rolls carried in a sub-frame. A push rod applies a vertical oscillating force to the sub-frame (which is carried on a swinging frame). A pair of strain guages are provided on the pushrod to detect the reaction of the timber plank. This plank is moved through the machine by causing the support rolls at the clamping stations to rotate. The oscillating forces is preferably applied at between 20 and 100 Hz. and are applied both positively and negatively.

17 Claims, 10 Drawing Figures

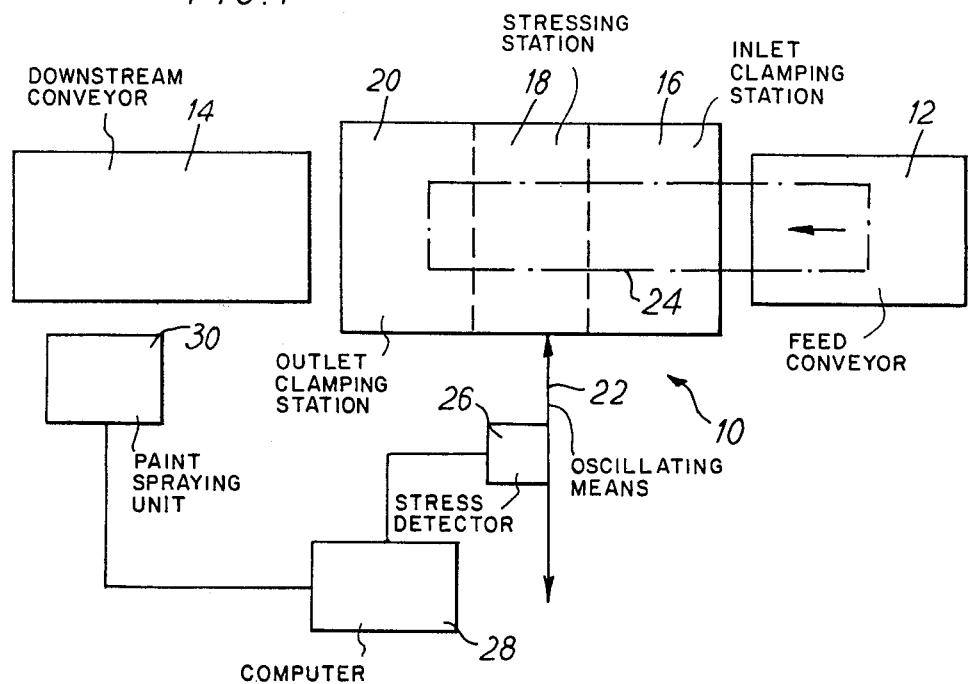
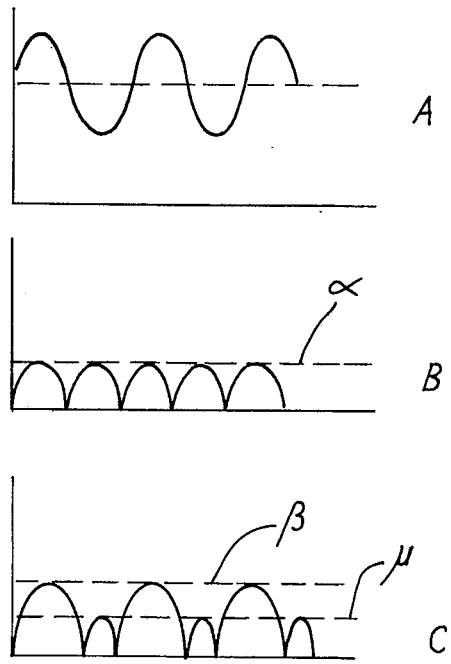

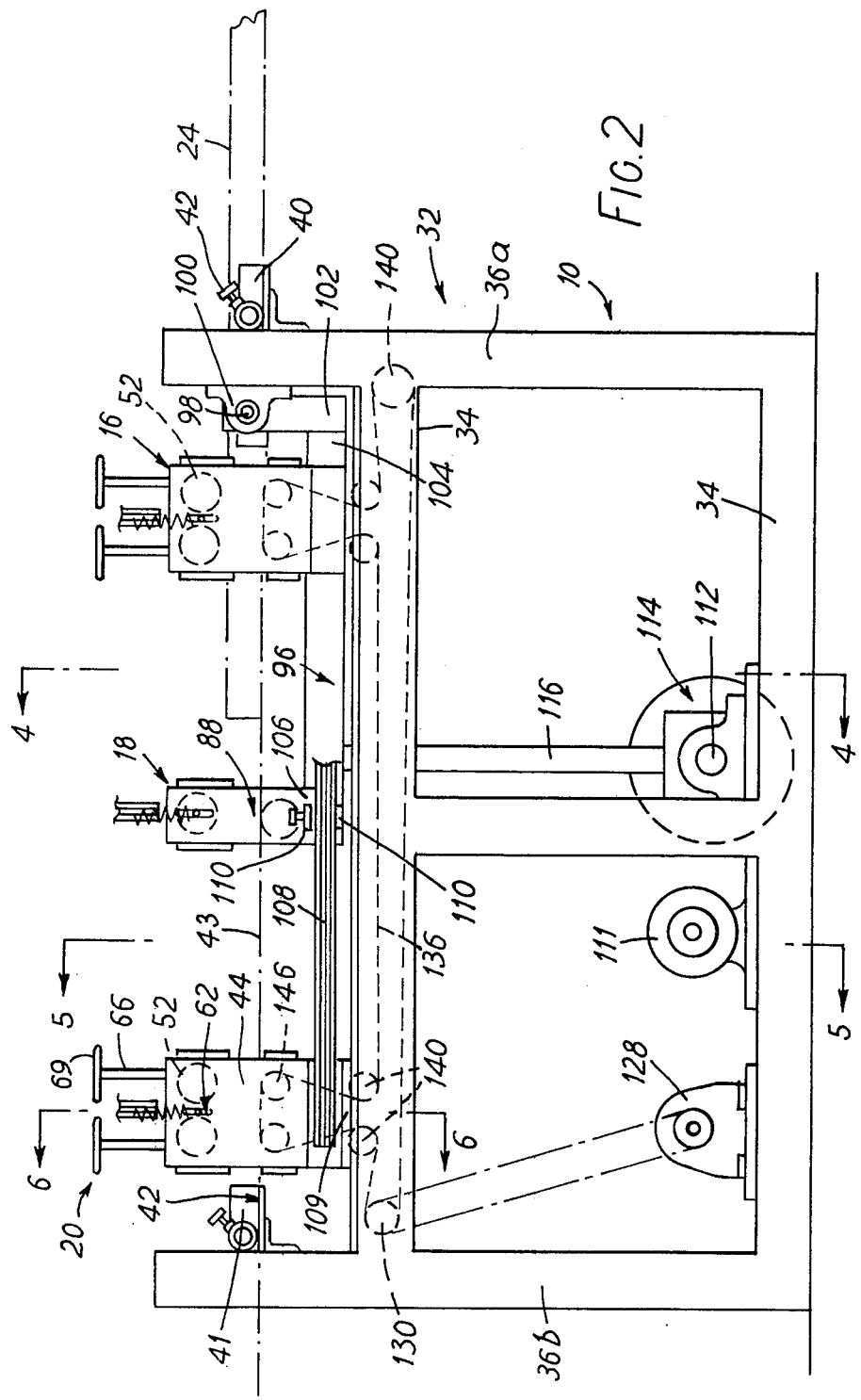

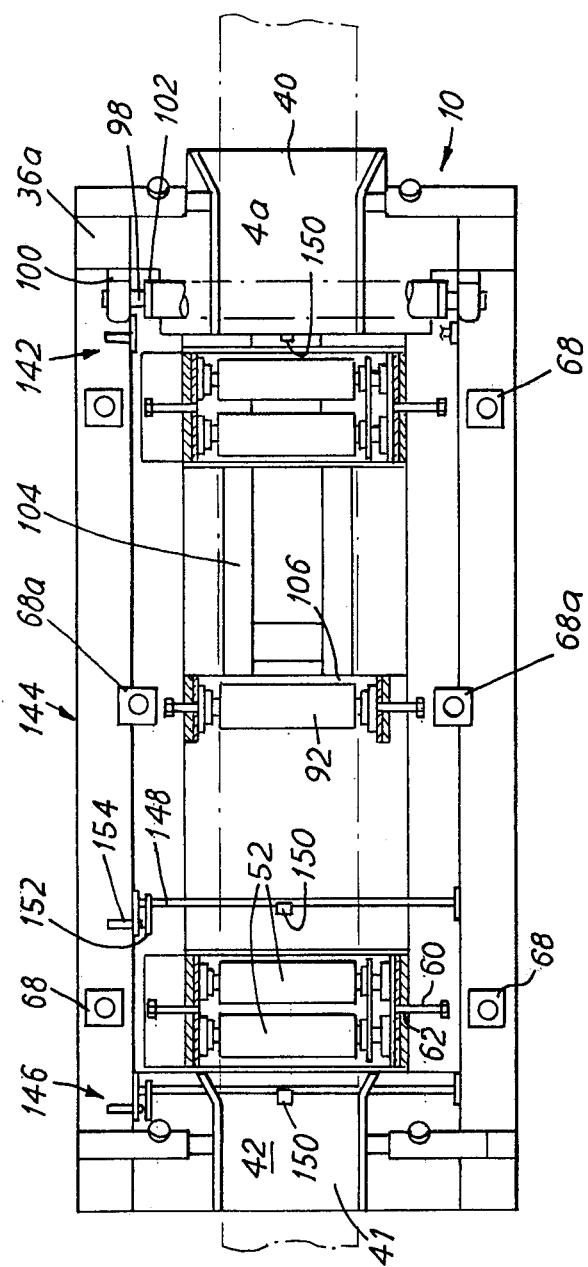

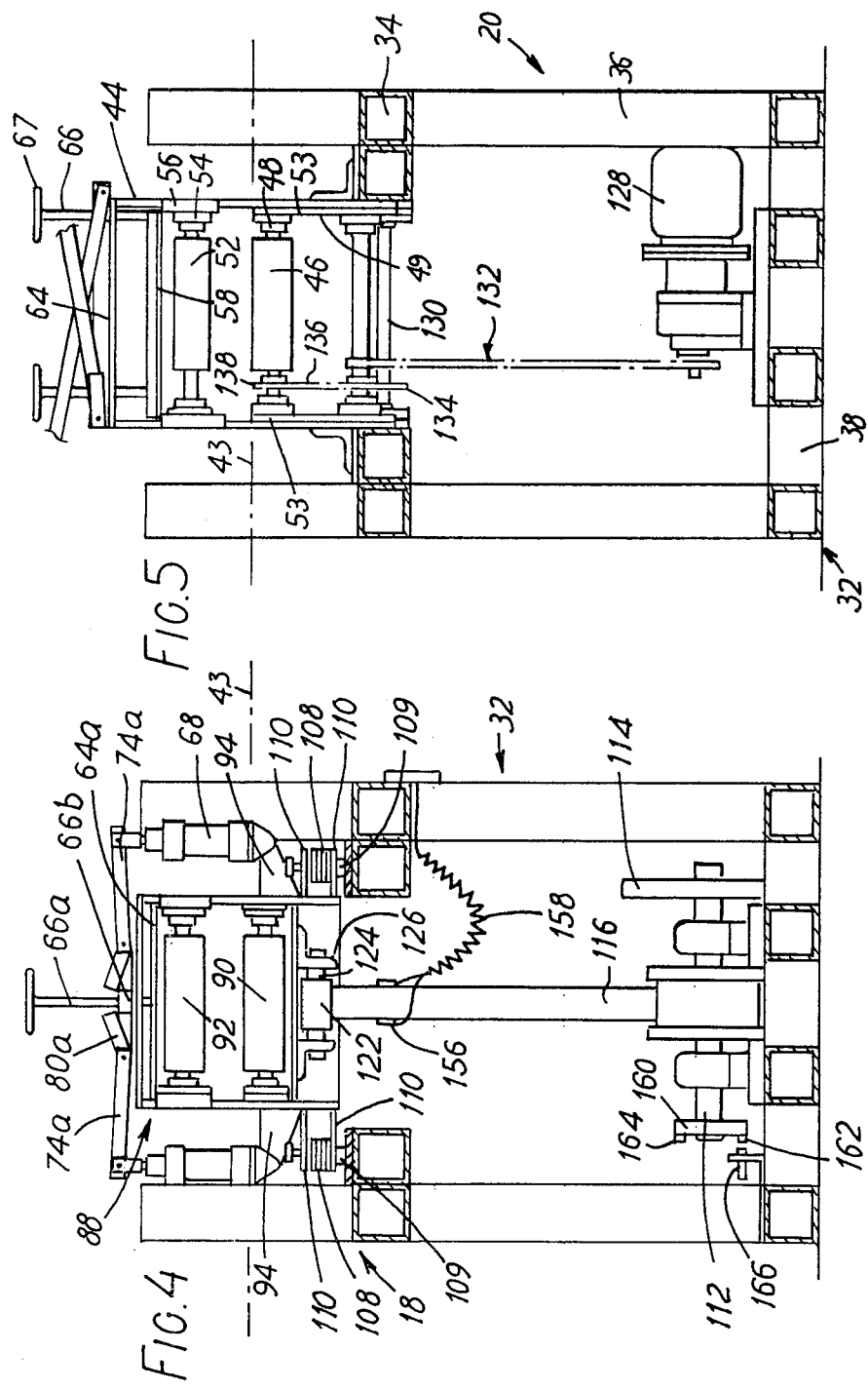

MECHANICAL STRESS GRADING OF TIMBER

This invention relates to methods of apparatus for mechanical stress grading of timber.

BACKGROUND TO THE INVENTION

Timber is used to a substantial extent in the construction industry. It is necessary that for this use the strength of the timber is known accurately. The dangers are obvious if the timber is too weak. On the other hand if adequate grading apparatus is not available, rough and ready techniques based on experience will often result in overgrading so that timber which is of adequate strength will be rejected.

A timber grader (as disclosed in South African patent specification No. 71/8601) has been developed to grade timber. The timber plank is placed on a pair of support rolls and pressure applied mid-way between the supports. The force needed for a particular deflection is measured to give an indication of the strength of the timber (as an alternative the deflection for a particular force may provide such indication). A timber plank is so tested at various positions along its length. In order to find the strength in the opposite direction, the plank has to be turned over and the measuring operation repeated. It will be seen that this process is very time consuming and can only be used as a sampling technique.

SHORT DESCRIPTION OF THE INVENTION

According to one aspect of the invention there is provided a method of mechanical stress grading of timber comprising applying an oscillating force to a length of timber which is moving longitudinally by a force applying means which is operatively connected to the timber through a linkage, wherein the method further comprises measuring the said force by determining the stress in a member within the linkage. The force may be applied with a fixed amplitude in which case only the force to cause the constant deflection may be measured. Alternatively the amplitude of the force may not be limited in which case both the amplitude and the force will be measured.

The method may further comprise measuring the dimensions of the section timber, normally at a location prior to the application of the oscillating force thereto, to enable the force measured to be related to the section of the timber.

According to another aspect of the invention there is provided apparatus for mechanical stress grading of timber comprising moving means for moving a length of timber along a path, oscillating means applying an oscillating force to timber moving along the path, clamping means for clamping the timber at location about the location at which the oscillating force is applied and force measuring means for measuring the force causing oscillation of the timber.

The oscillating means preferably comprises rotary force transmitting means in contact with the timber and connecting means connecting the rotary means to the force transmitting means, the arrangement being such that the force transmitting means oscillates through a fixed amplitude. The measuring means preferably comprises a strain gauge applied to a member forming part of the force transmitting means.

The rotary means preferably an eccentric device. The force transmitting means is preferably a push member and the strain gauge is preferably applied to the push member. If the push member is circular, the strain gauges may be located on opposite sides thereof. The force applying means preferably comprises at least one set of rollers between the nip of which the timber passes. The rotary means may alternatively comprise at least one rotating device having a part thereof out of round so as to apply the said oscillating force. Here again, the force applied means may comprise a pair of rolls which are preferably mounted in a sub-frame and preferably the strain gauge may be applied on a part of the sub-frame between a fixed roller and the rotary means which is conveniently an electric motor.

Preferably means are provided to ensure that the rolls forming the force transmitting means firmly grip the timber. Such means may comprise adjustment means to ensure that the nip between the rollers is of fixed-dimensions. Alternatively, and preferably, the said means may comprise pressure fluid jack means, preferably a pair of jacks, preferably pneumatic jacks forcing the rolls towards each other. Counter-balance means, such as a counter-balance spring, is conveniently provided to balance the weight of the frame. Biassing means are preferably also provided to increase the harmonic frequency of the frame so that its harmonic frequency is equal to the frequency of operation of the rotary means. Such biassing means preferably comprises spring means preferably carriage springs, preferably a pair of springs arranged on either side of the sub-frame. The biassing springs may also serve as the aforementioned counter-balance springs. The sub-frame is preferably mounted on a swingable carrier, both to limit the up and down movement of the sub-frame as well as to form a restraint against the horizontal forces imposed upon the rollers by the timber passing there through.

The clamping means preferably comprises two sets of rolls, conveniently each comprising two pairs of rolls are located on either side of the force transmitting rollers to restrain the timber during operation.

According to another aspect of the invention, there is provided apparatus for mechanical stress grading of timber comprising a path along which a length of timber is to be fed, two sets of fixed rolls located in the path between the nip of which a length of timber passing along the path will pass, a set of floating rolls mounted in a frame and located between the two sets of fixed rolls in such a way that the length of timber passing along the path will pass through the floating rollers, a driven shaft, an eccentric mounted on the driven shaft, a preferably vertical push rod having one end engaging the eccentric and the other end connected to the frame, strain gauge means mounted longitudinally on the push rod and electrical measuring device for measuring the output of the strain gauge whereby the timber length may be graded.

Preferably marking means are provided to mark the timber that has been graded, such marking means preferably comprising spray means to spray coloured paint in accordance with a colour code on to the timber.

Two embodiments of the invention will now be described by way of example with reference to the accompanying diagrammatic drawings.

BRIEF DESCRIPTION OF DRAWINGS

FIG. 1 is a block diagrammatic illustration of apparatus of the invention,

FIG. 2 is a side view of a timber grading device of the invention,

FIG. 3 is a plan of the device of FIG. 2,

FIG. 4 is a section on line 4—4 of FIG. 3,

FIG. 5 is a section on line 5—5 of FIG. 3 with certain parts omitted for clarity.

DESCRIPTION OF PREFERRED EMBODIMENT

General description

Figure 6:
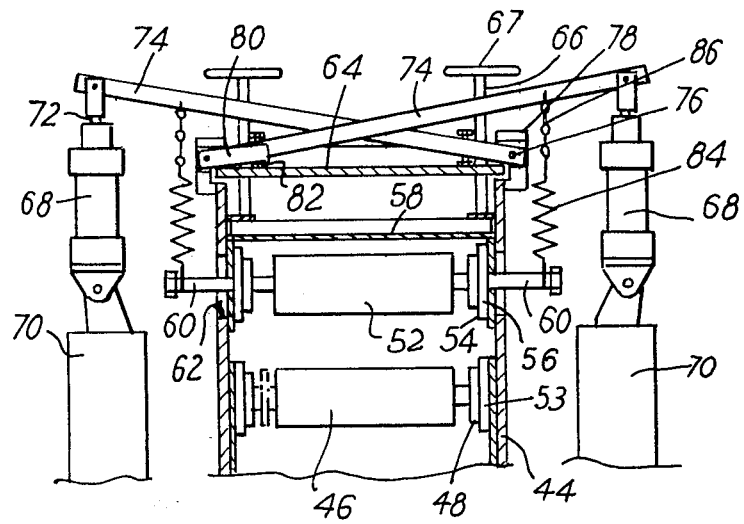
FIG. 6 is an enlarged detail section on line 6—6 of FIG. 3.
Figure 7:
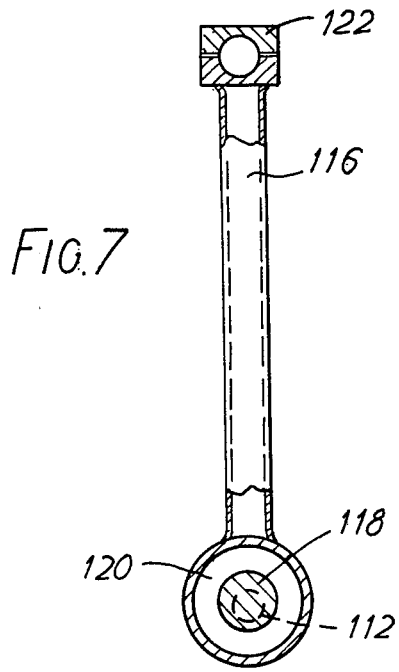
FIG. 7 is a view partially in section of the eccentrically mounted shaft.

Reference is first made to FIG. 1. A timber grading device 10 of the invention is located between a steel plate steel conveyor 12 and a downstream steel plate conveyor 14. The grading device 10 comprises an inlet roller clamping station 16, a stressing station 18 and an outlet clamping station 20. Timber feed means are provided to feed the timber plank 24 through the device 10.

Oscillating means 22 applies an oscillating force to a timber plank 24 when passing through the stressing station 18. Stress detector means indicated generally at 26 detects the reaction of the timber plank 24 to the oscillating force. The output signal of the detector means 26 is fed to a computer or processor 28 which gives a suitable output related to this signal. This output takes two forms, viz (a) a print out from the computer 28 and (b) a signal to a paint spraying unit 30.

The paint spraying unit 30 is located adjacent the downstream conveyor 14 and is arranged to paint a colour on to the edge of the timber plank. The colour applied will serve as a code for the timber. The arrangement of the computer 28 and the spraying unit 30, may be such that a single paint application to the plank may be provided indicating the plank's strength at its weakest point. Alternatively the spraying unit 30 may be caused to vary the paint colour applied to the plank edge or to paint only the weakest portions of the plank. Using this arrangement the timber processor may remove and discard weak lengths of timber so that the remaining strong lengths may be used for example by being finger jointed together.

THE TIMBER GRADING DEVICE

Reference is now made to FIGS. 2 to 7.

The timber grading device 10 comprises a main frame 32 formed of robust longitudinal, vertical and transverse square tube members (indicated generally at 34, 36 and 38 respectively).

An inlet gate unit 40, which is adjustable to guide timber of various widths, is carried on to the vertical members 36a nearest the feed conveyor 12. A similar unit 41 is carried on the vertical members 36b nearest the outlet conveyor 14 to guide the timber 24 on to that conveyor. The bases 42 of the units 40 are aligned and lie on a common plane 43.

The clamping stations 16 and 20 are located adjacent the inlet gate 40 and the unit 42 respectively.

THE CLAMPING STATIONS 16 AND 20

The inlet and outlet clamping stations 16 and 20 are identical. Therefore only the clamping station 20 will now be described.

The clamping station 20 comprises a "U"-section sub-frame 44 (see FIGS. 5 and 6). A pair of support rolls 46 span the arms of the sub-frame being journalled at their shaft ends in bearings 48 carried by fixed plates 24g secured to the arms. The rolls 46 lie under and tangential to the plane 43. A pair of clamping rolls 52 are located above the support rolls 46 respectively and have their ends journalled in bearings 54 carried by movable plates 56. These plates 56 are connected by an upper cross-member 58 and are also provided with projecting stubs 60 that pass through slots 62 in the arms for the purpose that will be described.

A floating top plate 64 is provided above the arms of the sub-frame 44 and is capable of moving up to about five millimeters from the sub-frame, being restrained from further upward movement by lugs (not shown). A pair of clamping screws 66 threadedly pass through the top plate 64 and act on the cross-member 58. Hand wheels 68 on the screws 66 facilitate manipulation thereof.

Pneumatic clamping means are provided to move the top plate (and hence the clamping rolls 52) downwardly. The clamping means comprises a pair of pneumatic jacks 68 pivotally mounted on lugs 70 projecting from the longitudinal members 34. The pistons 72 of the jacks 68 are connected respectively to the ends of two levers 74. Each lever 74 is pivotted on a pivot pin 76 supported by a lug 78 projecting from an arm of the sub-frame 44. Also carried by the pivot pin 76 is a presser arm 80 having an adjustable threaded foot 82 resting on the floating top plate 64.

Tension springs 84 are connected to the levers 74 respectively through connector chains 86 and are secured to the projecting stubs 60.

Many of the parts 54 to 86 are omitted from FIGS. 2 and 5 in the interest of clarity.

The clamping screws 66 are used to set the clamping rolls 52 a distance above the support rolls 46 slightly greater than the thickness of a plank of timber 24. When this setting has been completed the top plate 64 will have floated a maximum extent off the sub-frame 44.

When it is desired to move the clamping rolls 52 into their clamping position, the jacks 68 are contracted. This pivots the levers 74 downwardly and the presser arms 80 move the top plate 64 downwardly until it seats on the upper ends of the sub-frame arms. In so doing, the clamping rolls 52 are moved into a position to clamp the timber plank 24 against the support rolls 46.

On extending the jacks 68, the pressure on the top plate 64 will be removed and the plates 56 will be moved upwardly by the springs 84.

The pairs of support and clamping rolls 46 and 52 are horizontally spaced apart at any convenient distance to carry out the appropriate clamping operation as will be described above. As an indication however, these roll pairs may be spaced apart by 97 millimeters.

THE OSCILLATING STATION 29

The oscillating station includes a floating sub-frame 88 and oscillating means therefor.

THE FLOATING SUB-FRAME 88

The floating sub-frame 88 is located mid-way between the clamping stations 16 and 20. It comprises a "U"-shaped member that carries a support roll 90 and a clamping roll 92.

The mounting of these rolls 90 and 92 and clamping operation is substantially similar to the support and clamping rolls 46 and 52 at the clamping stations. However there is only a single central clamping screw 66a which is carried in a floating nut 66b located above the fixed top plate 64a of the frame and which screw passes freely through an opening in the top plate 64a. The clamping pneumatic jacks 68a are mounted on lugs 94 projecting from the arms of the sub-frame so as to be moveable with the sub-frame. These jacks 68a have connected to their piston rods, levers 74a respectively. Each lever 74a is pivotted on a pin carried by the top plate 64a and has a presser arm 80a lying above the floating nut 66b. As at the clamping stations, the initial position of the clamping roll 92 is set by the screw 66a. When the jacks 68a extend, the levers 74a are moved so that the presser arms 80a move the nut 66b downwardly thereby to move the clamping roll 92 into its clamping position.

The floating sub-frame 88 is mounted on a carrier 96 which is pivotally carried by transverse horizontal trunnions 98 journalled in plummer blocks 100 mounted on the vertical members 36a at the upstream end of the main frame 32.

The carrier 96 comprises a pair of vertical members 102 carrying the trunnions 98 at their upper ends and being secured to longitudinally extending members 104 that pass through the frame 44 of the inlet station 16 below the support rolls 46 and are joined by a transverse angle member 106 on which the sub-frame 88 is carried.

The coincident axes of the trunnions 98 lie in a plane which is located midway between the contact planes of the support and clamping rolls when the clamping rolls are clamping positions in their most closely adjusted positions.

The carrier 96 serves as a restraint for the sub-frame 88 against the horizontal forces imposed upon the rollers by the plank 24 passing through the oscillating station. It also serves to hold the sub-frame 88.

A pair of multi-leaf carriage springs 108 are mounted at their ends on spacer blocks 109 secured to the longitudinal frame members 34. Pairs of lugs 110 project from the sides of the floating sub-frame 88 and clamp therebelow the centres of the springs 108. These springs 108 serve to increase the natural or harmonic frequency of the oscillating unit (which comprises the floating sub-frame 88 and its carrier 96) to approach to the frequency of the oscillating means so as to minimize the forces that are required to oscillate the sub-frame 88. In addition the springs 108 are arranged to counter-balance the weight of the oscillating unit 88, 96 by being able to exert a greater upward than downward force on the unit.

THE OSCILLATING MEANS

The oscillating means comprises an electric motor 111 (hereinafter called the "oscillating motor") mounted on the bottom members of the main frame 32. The oscillating motor 111 drives a shaft 112 through a belt and pulley arrangement indicated generally at 114. This shaft 112 is located directly below the floating sub-frame 88 and carries thereon a vertical push rod 116 through the intermediary of an eccentric 118 having a short throw of conveniently 2,5 mm. The push rod 116 (best shown in FIG. 7) has a taper roller bearing 120 at its lower end to engage the eccentric and a plain metal bearing 122 at its upper end. This bearing 122 engages a horizontal transverse pin 124 carried between a pair of lugs 126 on the underside of the angle member 106 that carries the floating sub-frame 88. (In FIG. 2 the position of the push rod 116 is moved slightly for clarity.)

The eccentric 118 and push rod 116 are arranged so that when the eccentric 118 is midway between maximum or minimum throws, the support roll 90 is tangential to a plane 43 to which support rolls 46 are tangential. In this position the axis of the support roll 90 will be spaced at a suitable distance from the two innermost rolls 46 conveniently by 300 mm.

It will be seen that as the oscillating motor 110 rotates the shaft 112, the floating sub-frame 88 will be caused to oscillate up and down and consequently when a timber plank 24 is clamped in the floating sub-frame 88, to apply an oscillating force to the plank 24.

THE TIMBER FEED MEANS

An electric motor 128 (hereinafter called the "feed motor") drives an idler shaft 130 which is journalled between the upper longitudinal frame members 34, through a chain and sprocket arrangement indicated generally at 132. A further sprocket 134 (see FIG. 5) is carried by the shaft 130 and drives a drive chain 136. This drive chain 136 engages identically sized sprocket wheels 138 on the support rolls 46 at the clamping stations 16 and 20. Suitable idler sprockets 140 are provided to guide the drive chain 136 about the sprocket wheels 138 and into its return run.

THE PLANK SENSING MEANS

Three sensors 142, 144 and 146 are provided, sensor 142 upstream of station 16, sensor 144 between stations 18 and 20 and sensor 146 slightly downstream of the sub-frame at the station 20. Each sensor comprises a rotatable cross-shaft 148 which carries a first detector arm 150 and a second arm 152. The cross-shaft 148 is biassed to hold the arm 150 projecting into the path of the timber plank 24. A proximity switch 154 is located close to the second arm 152. When the detector arm 150 is moved downwardly by the plank 24, the cross-shaft 148 is rotated so that the arm 152 is moved into a position in which it lies adjacent the proximity switch 154.

The proximity switch 154 of sensor 142 is connected to the jacks 68 at inlet station 18 so that the clamping rolls 52 are moved to clamp the timber plank 24 shortly after it (the plank) has passed through the associated station. Further, the switch 154 will feed information to the processor 28 when released.

The sensor 144 operates similarly to cause the jacks 68 and 68a of stations 18 and 20 to clamp the timber plank. It will be understood that there is a delay between the proximity switches 154 being actuated and the jacks moving the clamping rolls their full movement of conveniently about 5 mm.

The sensor 146 feeds a signal to the processor when the plank 24 has just entered the outlet station 20.

THE STRESS DETECTOR MEANS

Secured at diametrically opposite parts of the surface of the push rod 116 near its upper end, and extending longitudinally of the push rod 116 are a pair of strain gauges 156. These strain gauges 156 are connected in series and also are connected by a loosely coiled wire 158 to the signal processor 28. The two strain gauges 156 will compensate for any twisting movement of the carrier 96 or the push rod 116.

The strain gauges 156 measure the forces in the push rod 116 which are the reaction forces due to the resistance to bending i.e. the strength of the timber plank.

Also mounted on the shaft 112 carrying the eccentric 118 is a disc 160. The disc 160 carries two steel pins 162 and 164. A proximity switch 166 is arranged adjacent the disc 160 to detect the location of the steel pins and to permit the transmission of the output of the strain gauges 156 to the signal processor only when the pins are adjacent the switch 166. The location of these pins 162 and 164 is such that they are adjacent the proximity switch 166 when the eccentric 118 is at maximum and minimum throw, i.e. when the plank 24 passing through the oscillating station is subject to maximum stress in a positive and negative direction.

The output signal of the strain gauge 106 is sinusoidal as shown in FIG. 10A. This signal is rectified in the processor 28 so that all the signals are positive (see FIG. 10B). Thus a straight line α can be drawn through all the points corresponding to the maximum stress gauges by the strain gauges 156 if the timber plank 24 is straight and of constant strength.

If however the plank 24 is bowed, alternate peaks will lie on spaced lines β and μ (see FIG. 10C), the spacing between the lines β and μ being equivalent to the amount of the bow. The strength of the timber will be given as the average of each two adjacent peaks. It will be understood that if for example there is a knot in the timber it is possible that the strength in one direction will be very high and in the opposite very low so that the average will be maintained. In such a case however the differences between the signals and the nearest alternate signals will indicate the existance of a weakness.

As mentioned above the output of the strain gauges 156 will be chopped by the proximity switch 166 so that only signals at the maximum amplitudes will be passed. For convenience the amplitude is converted into frequency. A counter (not shown) is provided for the peaks to provide an output proportional to the strength of the timber plank 24.

It will be understood that if the timber plank 24 has a weakness the amplitude of the strain gauges 156 output will drop. Consequently the frequency to which the output is converted will lessen and the counter will detect the drop to actuate the spray painter accordingly.

The operation of the apparatus 10 is as follows:

A length of timber 24 being moved along a path in the saw mills moves along the conveyor 12 in a longitudinal direction lying flat on the conveyor 12. The timber plank 24 enters the gate 42, engages the sensor 142 and passes through the inlet clamping station 16, the clamping roll 52 then clamping the timber plank 24 against the support rolls 46. The speed of rotation of the fixed rolls 46 now determines the speed of the timber plank 24. The timber then passes through the floating sub-frame 88 and thereafter actuates the sensor 144 actuating the pneumatic jacks at stations 18 and 20 so that the clamping rolls 92 and 46 clamps the timber plank 24. At this time the floating sub-frame 88 is already oscillating. The timber plank 24 as it exists from the outlet clamping station 20 and is clamped at station 16, 18 and 20 actuates sensor 146 which signals to the processor to receive the output of the strain gauges 156.

The grading of the timber now takes place as described above in the general description. As the timber plank 24 releases the sensor 142, the processor is signalled to cease grading. The sensors 142 and 144 when released permit the jacks to lift the upper rolls at the three stations thereby to release the timber.

MODIFIED FLOATING SUB-FRAME

Figure 8:
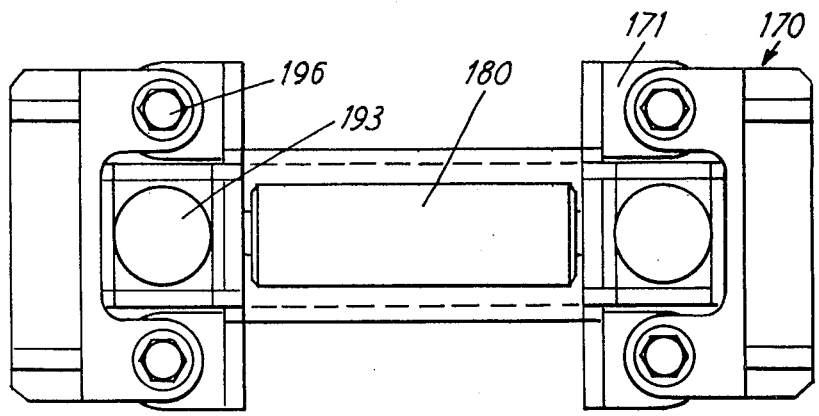
FIGS. 8 and 9 are respectively a plan and transverse section on line 9—9 of FIG. 8 of a modified floating sub-frame, and FIG. 10 are graphs showing how the signals are processed.
Figure 9:
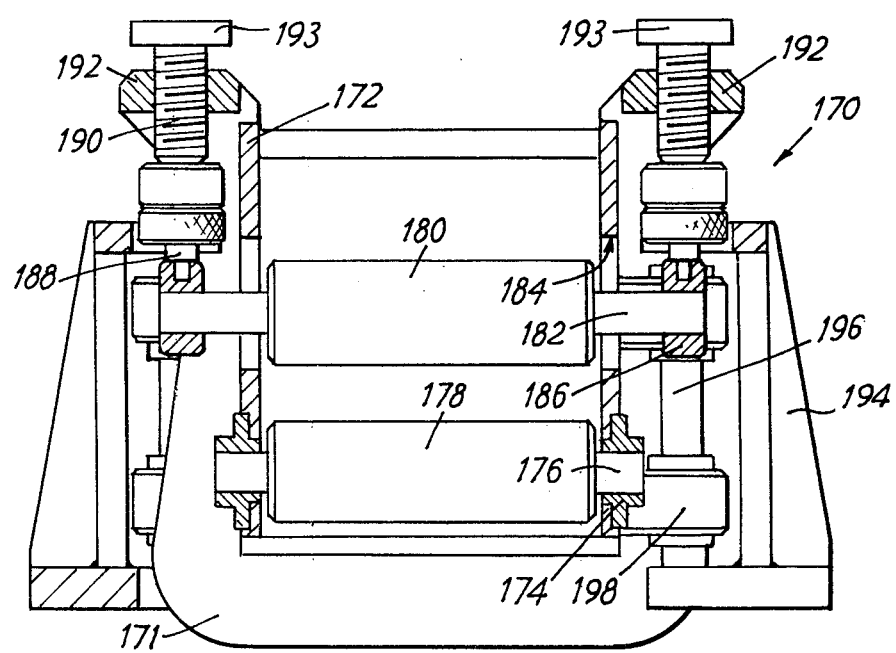

A modified floating sub-frame 170 (see FIGS. 8 and 9) comprises a robust "U"-member 171 carrying a pair of side arms 172. A pair of fixed bosses 174 are carried at the lower end of the side arms 172 and the shaft 176 on which the support rollers 178 are rotatably mounted is carried in these bosses 174. A clamping roll 180 is rotatably mounted on a longer shaft 182 parallel and directly above the support roll 178. The ends of the clamping roll shaft 182 project through slots 184 formed in the side arms. The free ends of the shaft 182 are carried in support blocks 186 that are mounted on the piston rods 188 of hydraulic jacks 190 located respectively on either side of the "U" member 171. The exterior of cylinders of the jacks 190 are threaded to engage threaded bores in lugs 192 on the "U"-member. Hand wheels 192 facilitate rotation of the jack cylinder.

The "U"-member 171 is carried by a pair of support posts 194 by means of adjusting screws 196 that engage side lugs 198 on the "U"-member 171. These posts 194 are secured to the oscillating carrier 96. The adjusting screws 196 permit adjustment of the position of the "U"-member 171 and hence the rolls 178 and 180 relative to the oscillating sub-frame 170.

Initial adjustment of the clamping roll 180 is effected by rotating the jack cylinder. The final clamping movement of this roll 180 which as in the first described embodiment is about 5 mm, is effected by the jacks 190.

The clamping stations may be similarly constructed with modifications as will be apparent to those skilled in the art.

The invention is not limited to the specific embodiments described above and illustrated in the drawings.

For example, one or more out of balance electric motors may be mounted on to the floating sub-frame 88 to provide the oscillating movement described above. In such an arrangement, there will be a fixed portion of the sub-frame 88 between the out of balance motor and the journalled ends of the support rolls and the strain gauge will be applied to this fixed portion. This will normally mean that the out of balance motors will be on the under side of the floating sub-frame whilst the pneumatic jacks will be on the upper side. In this case both the amplitude of the oscillations applied and the output of the strain gauge which will be a measurement of the resistance to such movement of the timber, will have to be measured and output computed in the signal device. This arrangement is of value particularly where the timber is curved.

A measuring device may also be provided at the gate 40 to measure the section of the timber. The output of the measuring device would be fed into the signal member to give a signal related to the section of the timber as well as to its strength.

The distance between the various sub-frames and the rolls at the clamping stations can be varied as desired within the limits imposed by the mechanical size of the parts.

The processor may actuate apparatus other than a spray painter as mentioned above. A set of tension springs mounted on the frame may be provided to counter-balance the weight of the unit 88 and 96 instead of the carriage springs 108 carrying out this additional function.

CONCLUSIONS

I have found that the apparatus described above gives a repeatable measurement of the strength of the timber and once properly calibrated (which can be relatively easily effected) gives very accurate measurements of this strength. It also has the advantages of being an in-line device capable of high speed grading of timber. It is further economical to construct and operate compared with currently available commercial timber grading machines. In addition it applies stresses in both directions which gives improved results.

I claim

1. A method of stress grading of timber comprising applying an oscillating force to a length of timber that is moving longitudinally by a force applying means which is operatively connected to the timber through a linkage, wherein the method further comprises measuring the said force by determining the stress in a member within the linkage.

2. A method as claimed in claim 1 further comprising actuating marking means in a manner related to the force measured.

3. A method as claimed in claim 1 comprising applying a holding force holding the timber against movement in the direction of the oscillating force, the holding force being applied at locations spaced from the location at which the oscillating force is applied.

4. Apparatus for mechanical stress grading of timber comprising:
   (a) moving means for moving a length of timber along a path,
   (b) oscillating means applying an oscillating force at a location to the said length of timber while moving along the path,
   (c) clamping means clamping the said length of timber at locations about the location at which the oscillating force is applied, and
   (d) force measuring means for measuring the force causing oscillation of the timber.

5. Apparatus as claimed in claim 4 wherein the oscillating means comprises:
   (a) rotary means,
   (b) force transmitting means in contact with the timber, and
   (c) connecting means connecting the rotary means to the force transmitting means, the arrangement being such that the force transmitting means oscillates through a fixed amplitude.

6. Apparatus as claimed in claim 4 wherein the force measuring means includes a strain gauge applied to a member forming part of the force transmitting means.

7. Apparatus as claimed in claim 6 wherein the said member is of circular section and wherein the force measuring means comprises a pair of strain gauges applied to the said member at diametrically opposed locations.

8. Apparatus as claimed in claim 6 in which the said member is a vertical push rod.

9. Apparatus as claimed in claim 4 in which the force applying means comprises a sub-frame and carried by the sub-frame a set of rolls between the nip of which the said timber passes.

10. Apparatus as claimed in claim 9 further comprising fluid jack means operatively connected to at least one of the said set of rolls forcing the rollers to move the rolls towards each other to engage the timber in the nip therebetween.

11. Apparatus as claimed in claim 9 comprising biassing means operatively connected to the sub-frame to reduce the harmonic frequency of the said sub-frame.

12. Apparatus as claimed in claim 11 in which the biassing means comprises a pair of carriage springs located on either side of the sub-frame.

13. Apparatus as claimed in claim 9 further comprising a swingable carrier on which the sub-frame is mounted.

14. Apparatus as claimed in claim 4 in which the clamping means comprises two sets of rolls located on either side of the force transmitting means to restrain the timber during the application of the oscillating force thereto.

15. Apparatus for mechanical stress grading of timber comprising:
   (a) a path along which a length of timber is to be fed,
   (b) two sets of fixed rolls which are located in the said path and between the nip of which a length of timber will pass,
   (c) a set of floating rolls mounted in a frame and located between the said two sets of fixed rolls at such a location that the length of timber passing along the path passes through the floating rolls,
   (d) a driven shaft,
   (e) an eccentric mounted on the driven shaft,
   (f) a push rod having one end engaging the eccentric and the other end connected to the frame,
   (g) strain gauge means mounted longitudinally on the push rod, and
   (h) an electric measuring device operatively connected to the strain gauge and giving signals relating to the output of the strain gauge.

16. Apparatus as claimed in claim 15 further comprising marking means for marking the timber, which marking means is operatively connected to the electric measuring device to be actuated to mark the timber in accordance with the signal from the said electric measuring device.

17. Apparatus as claimed in claim 16 wherein the marking means comprises painting means to paint the timber with a selected one of a number of paints of different color.

* * * * *